United States Patent [19]

Coenen et al.

[11] Patent Number: 4,794,178

[45] Date of Patent: Dec. 27, 1988

[54] PROCESS FOR THE PRODUCTION OF $^{18}$F-LABELED ORGANIC COMPOUNDS BY NUCLEOPHILIC SUBSTITUTION

[75] Inventors: Heinrich H. Coenen, Grevenbroich; Kurt Hamacher, Aachen/Kornelienmünster; Manfred Schüller, Jülich; Gerhard Stöcklin, Titz-Kalrath; Bernd Klatte; Arndt Knöchel, both of Hamburg, all of Fed. Rep. of Germany

[73] Assignee: Kernforschungsanlage Julich Gesellschaft mit beschrankter Haftung, Julich, Fed. Rep. of Germany

[21] Appl. No.: 752,413

[22] Filed: Jul. 5, 1985

[30] Foreign Application Priority Data

Jul. 4, 1984 [DE] Fed. Rep. of Germany ....... 3424525

[51] Int. Cl.$^4$ ............................ C07H 1/00; C07B 39/00
[52] U.S. Cl. ...................................... 536/122; 536/18.4; 536/18.5; 536/124; 260/408; 260/694
[58] Field of Search ............... 260/694, 408; 536/122, 536/18.4, 18.5, 124

[56] References Cited

U.S. PATENT DOCUMENTS

| | | |
|---|---|---|
| 4,001,291 | 1/1977 | Adolph ........................... 260/455 R |
| 4,150,292 | 4/1979 | Ter-Pogossian .................. 250/363 S |
| 4,309,611 | 1/1982 | Tanaka et al. ................... 250/363 S |
| 4,352,018 | 9/1982 | Tanaka et al. ................... 250/363 S |
| 4,392,996 | 7/1983 | Sternberger ..................... 260/112 R |
| 4,415,807 | 11/1983 | Friauf et al. .................... 250/363 S |
| 4,514,377 | 4/1985 | Symons et al. .................. 423/648 A |
| 4,514,562 | 4/1985 | Toscano .......................... 536/122 |
| 4,515,972 | 5/1985 | Das et al. ........................ 549/229 |
| 4,542,209 | 9/1985 | Takahara et al. ................. 536/122 |
| 4,617,386 | 10/1986 | Elmaleh et al. .................. 536/122 |

FOREIGN PATENT DOCUMENTS 2024222 1/1980 United Kingdom ............... 260/694

*Primary Examiner*—J. R. Brown
*Assistant Examiner*—Elli Peselev
*Attorney, Agent, or Firm*—Nils H. Ljungman

[57] ABSTRACT

Organic compounds labeled with no-carrier-added fluorine 18 are processed to yield a compound having a formula in the form of $^{18}$F-R through a nucleophilic substitution reaction. The process has a series of steps. The first step of the process relates to providing an organic compound having a formula of X-R. X is the nucleophilic leaving group in the substitution action, and R is a preferred substituted hydrocarbon structure being selected from aliphatic, alicyclic, heterocyclic aliphatic, carbocyclic and heterocyclic aromatic structures. The X-R compounds with acid hydrogen are excluded. The next step is to bring the organic compound X-R into contact with fluoride ions which are present in a solvent. These fluoride ions are essentially carrier free $^{18}$F ions. The organic compound is brought into contact with the fluoride ions in an apparatus to produce a reaction. The reacting mixture comes into contact during reaction only with surfaces in the apparatus which are made of metals as copper, stainless steel, platinum and Inconel and preferably of glassy carbon. In one embodiment, the reaction takes place at a temperature of between 100° C. and 150° C. in the presence of a basic alkali salt which is contained in a acetamide melt. The reaction may alternately take place in a preferred embodiment, in solution, in a moderately polar, aprotic solvent in the presence of a macrocyclic polyether and an alkali salt at a temperature in the range of 50° C. to 150° C.

4 Claims, No Drawings

PROCESS FOR THE PRODUCTION OF $^{18}$F-LABELED ORGANIC COMPOUNDS BY NUCLEOPHILIC SUBSTITUTION

BACKGROUND OF THE INVENTION

1. Field of the Invention

The invention relates generally to $^{18}$F labeling of organic compounds and, more particularly, to a process for the production of $^{18}$F-labeled organic compounds by nucleophilic exchange.

2. Description of the Prior Art

The production of compounds labeled with fluorine-18 has for years been the focus of radiopharmaceutical research for nuclear medicine and functional diagnosis. This is because of the optimal nuclear properties of fluorine-18 for positron emission tomography (PET). The positron emitter, fluorine-18, is more advantageous to use in many applications than other radionuclides, as a means by which covalently-bonded fluorine compounds can be labeled. Fluorine-18, because of its decay energy (0.64 MeV), allows the highest inherent resolution during PET measurements (without interfering secondry lines). In addition, fluorine-18 has a relatively convenient half life, $T_{1/2}$, of 109.7 minutes.

Carrier-free or labeled compounds of extremely high specific activity of more than 1000 curies/mmol are especially necessary for in vivo receptor studies, and in all cases where, for toxicological reasons or not to disturb sensitive biological equilibria, an in vivo application in the subnanomolar or picomolar region is necessary. Electrophilic processes have all recently been based on labeled molecular fluorine ($F_2$). However, the molecular fluorine inherently contains inactive fluorine carriers with the resultant problems ensuing therefrom. The nucleophilic substitution with fluoride essentially makes possible an introduction of $^{18}$F without or if any only extremely small quantities of carrier substances. The problems of reactions with fluoride lie in its extremely high charge density and hydrophilic properties, which cause a weak nucleophilic action and high adsorption losses, especially when working without a carrier additive. Reactions which utilize carrier-free fluoride therefore generally require the careful exclusion of water.

Previous investigations have attempted to increase the reactivity of ammonium or alkali fluorides by the addition of phase transfer catalyst, such as long-chain onium salts and cyclic polyethers (crown ethers), or by the addition of silver oxide, as well as by the use of easily-substitutable leaving groups such as tosylates and triflates. Except for a few cases, production without the addition of carriers was so far possible only with simple alkyl compounds, and even then produced only small yields (less than 20%). Higher yields were obtained only with fluoroethanol, methyl fluoride and simple aromatic molecules, substituted benzols, with the latter by the replacement of the nitro-group in DMSO, at relatively high temperatures of 150° C. with Rb$^{18}$F. DMSO is dimethyl sulfoxide, which is described in U.S. Pat. No. 4,514,377, which patent is incorporated herein by reference.

OBJECT OF THE INVENTION

The object of the invention is therefore to increase the yields of $^{18}$F compounds when processed carrier-free or without carriers (no-carrier-added). This object is primarily achieved by the nucleophilic substitution reaction being conducted in an apparatus which has surfaces with which the reaction mixture comes into contact which are made from predetermined metals such as copper, platinum, stainless steel, Inconel ® (Ni base alloys manufactured by INCO, Canada), or most preferably from glassy or vitreous carbon glass (pyro carbon) such as Sigradur ® G, L or K. Sigradur carbon glasses are manufactured by Sigri Elektrographit GMBH, Meitingen, Federal Republic of Germany. The superscript ® indicates that the item is identified by a trademark which is registered in a trademark register.

SUMMARY OF THE INVENTION

The invention resides broadly in a process for labeling organic compounds with fluorine 18, the process comprising the steps of: providing an organic compound having a formula of X-R, wherein R is an arbitrarily substituted hydrocarbon structure being selected from the group consisting of aliphatic, alicyclic, heterocyclic aliphatic, carbocyclic and heterocyclic aromatic structures substituted whatever but excluding H-acid compounds, wherein X is a nucleophilic leaving group; and contacting said organic compound with fluoride ions in a solvent, wherein the fluoride ions are essentially free ions, the organic compound being contacted with the fluoride ions in an apparatus, all surfaces of which making contact with the reaction mixture, consist of predetermined metal or especially of glassy carbon whereby compounds having the formula $^{18}$F-R are produced.

The predetermined metal may be selected from the group consisting essentially of copper, stainless steel, platinum and Inconel.

Yet another aspect of the invention deals with the above process wherein X is selected from the group consisting of halogens and pseudohalogens and when R is an aliphatic hydrocarbon structure especially of -OTos and -OTf, where Tos is tosylate and Tf is triflate or else. Tosylate is described in U.S. Pat. No. 4,515,972, which is incorporated herein by reference. Triflates are described in U.S. Pat. No. 4,001,291, which is also incorporated herein by reference. An example of a pseudohalogen is a cyanogen.

A further aspect of the invention deals with the above process wherein R is an aromatic hydrocarbon structure; in this case X preferably may be selected from -NO$_2$ and -N+(alkyl)$_3$.

A yet further aspect of the invention deals with the above process wherein the solvent is an acetamide liquified material containing a basic alkali salt.

An additional aspect of the invention deals with the above process wherein said basic alkali salt is a member of the group consisting of Na$_2$CO$_3$, K$_2$Co$_3$, Rb$_2$CO$_3$ and Cs$_2$CO$_3$.

An additional further aspect of the invention deals with the above process wherein the organic compound is contacted with the fluoride ions between about 100° C and about 150° C.

A yet additional aspect of the invention deals with the above process wherein the solvent is a moderately polar, aprotic solvent which further contains the complex of a basic nonnucleophile alkali salt and macrocyclic polyether.

Another aspect of the invention deals with the above process wherein the polyether is an aminopolyether.

Yet another aspect of the invention deals with the above process wherein the aminopolyether is a 2.2.2 aminopolyether and the salt is $K_2CO_3$.

A further aspect of the invention deals with the above process wherein the organic compound is contacted with the fluoride ions in the moderately polar, aprotic solvent at between about 50° C. and about 150° C.

DETAILED DESCRIPTION OF THE PREFERRED EMBODIMENTS

The reaction is thereby preferably conducted either in liquefied acetamide material containing a basic alkali salt, specifically $Na_2CO_3$, $K_2CO_3$, $Rb_2CO_3$ or $Cs_2CO_3$ at 100° to 150° C., or preferably at 50° to 150° C. in a homogeneous phase with an aminopolyether, such as Kryptofix ® 2 2 2, - complexed $K_2CO_3$, especially in acetonitril and/or DMSO as a solvent. Kryptofix ® is manufactured by Merck, Darmstadt, Federal Republic of Germany.

According to the invention, secondary reactions are prevented, wall losses are almost completely eliminated, and surprisingly high yields (up to 95%) are achieved. The reaction in aprotic solvents with aminopolyether is also only insignificantly adversely affected by traces of water. Such traces of water are herein meant to include quantities of up to about 1%.

The invention comprises the following improvements:

1. Exclusion of Adsorption Losses

Since high adsorption losses always occur in the reaction of fluoride without the addition of a carrier, the total yield, in relation to the $^{18}F$ fluoride produeed in the reactor or accelerator, is sometimes drastically reduced. Systematic studies of various wall materials for reaction vessels showed that copper, stainless steel and Inconel ® result in approximately 10% wall losses, and glassy carbon results in less than 2% wall loss. The use of these materials, especially of glassy carbon, made possible $^{18}F$ fluorination without a carrier of the above compounds with—up to now not achieved—total radiochemical yields of 60-95% under less violent reaction conditions than heretofore. The use of glassy carbon was shown to be especially desirable because of the very low wall loss. Fluorinations in inert vessels usually used heretofore, such as Teflon, likewise may result in low wall losses, but lead to lower exchange yields. When Teflon is used, the poor handling and the low heat conductivity of the material are causes of longer synthesis times and thus a loss of radioactivity.

2. Improvement of the Conversion (a) By the addition of basic alkali salts of low nucleophilic action, specifically $Na_2Co_3$, $K_2CO_3$, $Rb_2CO_3$, $Cs_2CO_3$ to liquefied acetamide material at 100°-150° C., the exchange of the dissolved fluoride could be increased, without the addition of a carrier with alkyl compounds, especially with compounds comprising long-chain ω-halogen fatty acids and suitably-protected sugars, from 0% to 70% radiochemical yields. Significant $^{18}F$-labeled radiopharmaceuticals for use with PET are known and available in both long-chain ω-halogen fatty acids and suitably-protected sugar compounds—see examples herein.

(b) As a most preferred alternative, in a homogeneous solution of (optimal) acetonitril, which contained a complex of aminopolyether 2.2.2. (Kryptofix ®) with $K_2CO_3$, 60% to 95% of carrier-free $^{18}F$ fluoride was converted with these same alkyl compounds during reflux. The special suitability of this reaction mixture lies in the optimal cation-polyether combination and the use of equimolar quantities of aminopolyether and alkali cations. In addition to the cation-polyether combination, complexes of other metal cations and corresponding polyethers were similarly well suited for the reaction.

These reaction solutions as described above in (a) and (b) are likewise suited for nucleophilic fluorine exchange with aromatic compounds, whereupon, in comparison with prior methods, significant advantages of the present invention are represented in that, other than $—NO_2$, halogens may be used as the leaving groups. A further advantage of the process is the lower reaction temperature. This feature of the invention is especially important for the carrier-free production of complex $^{18}F$-labeled receptor ligands for the in vivo measurement of receptor densities by means of PET. One important example is neuroleptics of the butyrophenon series, such as spiroperidol, methylspiroperidol, benperidol, etc., which have one fluorine atom in the pharmocophoric group. The specific activities to be attained for all the compuunds described are greater than $1.5 \times 10^4$ curies/mmol.

Some examples of positron emission tomography are described in U.S. Pat. Nos. 4,415,807; 4,352,018; 4,309,611; and 4,150,292, which patents are incorporated herein by reference.

EXAMPLES

Example 1

$[^{18}F]$-17-Fluoroheptadecanoic acid (17-$^{18}F$-HdA) where HdA means fluoroheptadecanoic acid.
for A: acetamide melt 2-5 ml of twice-distilled water containing $^{18}F$-ions and 10 mg $K_2CO_3$ were evaporated until dry at 180° C. in a helium flow (approximately 50 ml min) in a cylindrical Sigradur ®-G vessel with a capacity of approximately 10 ml, and then heated for another 15 minutes at 180° C. in the helium flow and then cooled in the helium flow. 100 mg of acetamide and 20-120 mg 17-bromineheptadecanoic acid methylester were added. The reaction vessel is closed by means of a V4A type stainless steel plug and a Sigraflex ® gasket. Sigraflex is manufactured by Sigri Elektrographit GMBH, Meitingen, Federal Republic of Germany. The reaction time was 10-20 minutes at 100°-150° C. in an oil bath accompanied by agitation. After cooling, 2 ml of 5n methanolic KOH were added, and then the agitated mixture was heated for 15 minutes at 70° C. in an oil bath.

After addition of 10 ml $H_2O$ and 3 ml 15% $H_2SO_4$, repeated extraction with 10 ml or 5 ml n-heptane at 80° C. was performed. The heptane phases are vaporized until dryness and the $[^{18}F]$-17-fluoroheptadecanoic acid transferred in 2 ml eluent and isolated by means of high-pressure liquid chromotography.

High pressure liquid chromotography is described in the work of the same name authored by Phyllis Brown; published by Academic Press, 1973, and is incorporated herein by reference. Liquid chromatography is described in U.S. Pat. No. 4,392,996, which is also incorporated herein by reference.

High pressure liquid chromotography (HPLC) was performed in a chromatography column filled with Nucleosil C-18 which had a grain size of 7.5 μm. Nucleosil C-18 designates a filling on a base of silica gel, derived with a C-18 alkyl. The chromotography column has a length of 25 cm and an inner diameter of 16 mm. The solution used was methanol, water, and acetic acid in a volume ratio of 896 parts methanol, to 100 parts water, to 4 parts acetic acid. The chromotography was carried out at a pressure of 43 bars and at a flow rate of 7.4 ml/min. k' (17-F-HdA) was equal to 2.64. This resulted in a yield of 17-$^{18}$F-HdA being 48±4%. This high pressure chromotography may be expressed in abbreviated form as follows:

Nucleosil C-18, 7.5 m; 25 cm; 16 mm i. $\phi$; methanol: Water: acetic acid 896:100:4 (v,v,v); 43 bar; 7.4 ml/min; k' (17-F-HdA) =2.64

Yield of 17-$^{18}$F-HdA: 92±3% Nucleosil ® is manufactured by Macherey Nagel & Co., Duren, Federal Republic of Germany.

EXAMPLE 2

For B: Aminopolyether acetonitril solution 2 to 5 ml of twice-distilled water containing $^{18}$F-ions and 2.3 mg $K_2CO_3$ and 12.6 mg aminopolyether 2.2.2 were placed in a cylindrical Sigradur ®-G vessel with a capacity of approximately 10 ml. At an oil bath temperature of approximately 110° C. and a temperature of approximately 90° C. in the reaction vessel, the solution is evaporated until dry in a helium flow of approximately 50 ml/min. Then 0.5 ml $CH_3CN$, (spectroscopically pure; dried over $Al_2O_3$, activity level I, active, neutral) and 10 mg 17-bromineheptadecanoic acid methylester are added and boiled in reflux for 10 minutes. Then there is an addition of 2 ml 5 n methanol KOH and reflux boiling for 15 minutes. The further preparation was as described for the acetamide melt from Example 1 as follows: After addition of 10 ml $H_2O$ and 3 ml 15% $H_2SO_4$, repeated extraction with 10 or 5 ml n-heptane at 80° C. was performed. The heptane phases were vaporized until dry and the [$^{18}$F]-17-fluoroheptadecanoic acid transferred in 2 ml eluent and were isolated by means of high-pressure liquid chromotography.

Yield: 92±3%.

EXAMPLE 3

[$^{18}$F]-2-fluoro-2-desoxy-D-glucose (2-$^{18}$FDG) where FDG signifies fluoro-2-desoxy-D-glucose for B: Aminopolyether-acetonitril solution The water containing $^{18}$F- was evaporated until dryness, as described in Example 2, in the presence of 2.2.2 aminopolyether and $K_2CO_3$. Then a solution of 20 mg 1.3.4.6-tetra-0-acetyl-2-O-trifluormethanesulfonyl-$\beta$-D-mannopyranose (dried preferably over Sicapent) in 1 ml acetonitril (see Example 2) was added and heated to boiling for 5 minutes. Then the solution was evaporated to approximately 0.5 ml in a helium flow and after dilution with about 5 ml water permeated through a SEP-PAK $C_{18}$ cartridge. The product/educt mixture was extracted with 2 ml THF (tetrahydrofuran) from the cartridge and the THF evapoated until dryness. The residue was hydrolyzed after the addition of 2 ml 1 molar hydrochloric acid for 15 minutes in reflux. To clean the product from hydrophobic by-products, HCl and unreacted $^{18}$F-, the solution of 2-$^{18}$FDG was filtered by means of a $C_{18}$ SEP PAK cartridge and then subjected to chromotogrpphy via a short column with ion-retarding resin (AG 11A8, BioRad) and aluminum oxide. Yield: 82±4%. SEP PAK is manufactured by Waters Associates, Maple Street, Melfort, Massachusetts 01757. AG 11A8, BioRad is manufactured by BioRad, Chemical Division, 200 Wright Avenue, Richmond, Calif. 94804.

The invention as described hereinabove in the context of the preferred embodiments is not to be taken as limited to all of the provided details thereof, since modifications and variations thereof may be made without departing from the spirit and scope of the invention.

What is claimed is:

1. A process for labeling organic compounds with fluorine 18, said process comprising the steps of:
   (a) providing an organic compound having a formula:

X-R wherein R is an arbitrarily substituted hydrocarbon structure, said hydrocarbon structure being selected from a member of the group consisting of aliphatic, alicyclic, heterocyclic aliphatic, carbocyclic and heterocyclic aromatic structures substituted wherever but excluding H-acid compounds, wherein X is a nucleophilic leaving group; and
   (b) contacting said organic compound with fluoride ions in a solvent, wherein said fluoride ions are essentially carrier free $^{18}$F ions;
   said solvent being a moderately polar, aprotic solvent which further contains homogeneously dissolved therein the complex of a basic non-nucleophile alkali salt and macrocyclic polyether.

2. The process as in claim 1 wherein said macrocyclic polyether is an aminopolyether.

3. The process as in claim 2 wherein said aminopolyether is a 2.2.2 aminopolyether.

4. The process as in claim 3 wherein said salt is $K_2CO_3$.

* * * * *